US012678148B2

(12) United States Patent
Goodman et al.

(10) Patent No.: US 12,678,148 B2
(45) Date of Patent: Jul. 14, 2026

(54) ADHESIVE APPLICATOR INCLUDING NOVEL APPLICATOR TIP

(71) Applicant: OKAPI MEDICAL, LLC, Akron, OH (US)

(72) Inventors: Jack Goodman, Ann Arbor, MI (US); David Kay, Akron, OH (US); Ananth Murthy, Akron, OH (US); Darren Obrigkeit, Aachen (DE); Gary Pennington, New Franklin, OH (US); Yizhou Zhao, Brighton, MA (US); Joseph Spalding, Elyria, OH (US); Jonathan Morgan, Westlake, OH (US); Michael Tracz, Brecksville, OH (US); Paul Wyman, Maastricht (NL)

(73) Assignee: OKAPI MEDICAL, LLC, Akron, OH (US)

( * ) Notice: Subject to any disclaimer, the term of this patent is extended or adjusted under 35 U.S.C. 154(b) by 571 days.

(21) Appl. No.: 18/010,128

(22) PCT Filed: Jun. 16, 2021

(86) PCT No.: PCT/US2021/037605
§ 371 (c)(1),
(2) Date: Dec. 13, 2022

(87) PCT Pub. No.: WO2021/257687
PCT Pub. Date: Dec. 23, 2021

(65) Prior Publication Data
US 2023/0233197 A1 Jul. 27, 2023

Related U.S. Application Data

(60) Provisional application No. 63/107,656, filed on Oct. 30, 2020, provisional application No. 63/041,488, filed on Jun. 19, 2020.

(51) Int. Cl.
*A61B 17/00* (2006.01)
*A61B 90/00* (2016.01)

(52) U.S. Cl.
CPC ................... *A61B 17/00491* (2013.01); *A61B 2017/00424* (2013.01); *A61B 2090/037* (2016.02); *A61B 2090/061* (2016.02)

(58) Field of Classification Search
CPC .... A61B 17/00491; A61B 2017/00424; A61B 2090/037; A61B 2090/061;
(Continued)

(56) References Cited

U.S. PATENT DOCUMENTS 2,721,858 A 10/1955 Joyner et al.
3,254,111 A 5/1966 Hawkins et al.
(Continued)

FOREIGN PATENT DOCUMENTS

DE 60126127 T2 11/2007
EP 1799609 B1 11/2013

OTHER PUBLICATIONS

JBC, DPM Manual Solder Paste Dispenser webpage capture May 3, 2022, https://www.jbctools.com/dpm-manual-solder-paste-dispenser-product-1946.html, publication date unknown, one webpage, JBC.
(Continued)

*Primary Examiner* — Andrew Restaino
(74) *Attorney, Agent, or Firm* — Hudak, Shunk & Farine Co. LPA

(57) ABSTRACT

An applicator is provided for a flowable media, particularly an adhesive contained in a container and the applicator includes an elongate body member having an internal cavity that holds the container. The cavity has a distal end with a breaking means that is actuated by an axial force. Various embodiments of the actuator are shown to apply the force, including a wire cracker and a molded integral handle
(Continued)

member with a lever linkage that bears against a ram which holds the ampoule and having a spring arm that rides within the cavity to oppose a pivoting force on the handle. These embodiments also enable single handed use.

18 Claims, 10 Drawing Sheets

(58) Field of Classification Search
CPC ...... A61B 2017/00495; A61B 17/0057; A61B 2017/00115; A61B 2017/0053; A61B 2017/00539; A61B 2017/00623; A61B 2017/00654; A61B 2017/00659; A61B 2017/00893; A61M 5/00; A61M 5/3294; A61M 37/0069; A61M 2005/005; A61M 2005/2485
See application file for complete search history.

(56) References Cited

U.S. PATENT DOCUMENTS

| | | | |
|---|---|---|---|
| 3,940,362 A | | 2/1976 | Overhults |
| 3,995,641 A | | 12/1976 | Kronenthal et al. |
| 4,304,869 A | | 12/1981 | Dyke |
| 4,313,865 A | | 2/1982 | Teramoto et al. |
| 4,364,876 A | | 12/1982 | Kimura et al. |
| 4,461,837 A | * | 7/1984 | Karle ....................... C12Q 1/22 |
| | | | 435/31 |
| 4,528,268 A | * | 7/1985 | Andersen ................. C12Q 1/22 |
| | | | 435/31 |
| 4,560,723 A | | 12/1985 | Millet et al. |
| 4,720,513 A | | 1/1988 | Kameyama et al. |
| 5,130,369 A | | 7/1992 | Hughes et al. |
| 5,216,096 A | | 6/1993 | Hattori et al. |
| 5,328,687 A | | 7/1994 | Leung et al. |
| 5,439,468 A | * | 8/1995 | Schulze ............. A61B 17/1285 |
| | | | 227/19 |
| 5,445,462 A | * | 8/1995 | Johnson .............. A61M 35/006 |
| | | | 401/133 |
| 5,514,371 A | | 5/1996 | Leung et al. |
| 5,514,372 A | | 5/1996 | Leung et al. |
| 5,575,997 A | | 11/1996 | Leung et al. |
| 5,582,834 A | | 12/1996 | Leung et al. |
| 5,624,669 A | | 4/1997 | Leung et al. |
| 5,928,611 A | | 7/1999 | Leung |
| 6,143,352 A | | 11/2000 | Clark et al. |
| 6,143,805 A | | 11/2000 | Hickey et al. |
| 6,183,593 B1 | | 2/2001 | Narang et al. |
| 6,217,603 B1 | | 4/2001 | Clark et al. |
| 6,310,166 B1 | | 10/2001 | Hickey et al. |
| 6,455,064 B1 | | 9/2002 | Narang et al. |
| 6,512,023 B1 | | 1/2003 | Malofsky et al. |
| 6,536,975 B1 | | 3/2003 | Tufts |
| 6,547,467 B2 | | 4/2003 | Quintero |
| 6,579,469 B1 | | 6/2003 | Nicholson et al. |
| 6,620,846 B1 | | 9/2003 | Jonn et al. |
| 6,705,790 B2 | | 3/2004 | Quintero et al. |
| 6,779,657 B2 | | 8/2004 | Mainwaring et al. |
| D500,085 S | | 12/2004 | Cotter et al. |
| 6,960,040 B2 | | 11/2005 | D'Alessio et al. |
| 7,306,390 B2 | | 12/2007 | Quintero et al. |
| 7,338,477 B2 | * | 3/2008 | Meyer .................. A61F 9/0017 |
| | | | 604/289 |
| 7,516,872 B2 | | 4/2009 | Boone et al. |
| 8,287,202 B2 | | 10/2012 | Goodman et al. |
| 8,376,642 B2 | | 2/2013 | Quintero et al. |
| 8,431,666 B2 | | 4/2013 | Kennedy et al. |
| D706,644 S | | 6/2014 | Ruiz, Sr. et al. |
| 8,790,032 B2 | | 7/2014 | Quintero et al. |
| 8,808,620 B1 | | 8/2014 | Chu et al. |
| 8,852,231 B2 | | 10/2014 | Mach et al. |
| 8,980,947 B2 | | 3/2015 | Zhang et al. |
| 9,066,711 B2 | | 6/2015 | Ruiz, Sr. et al. |
| 9,430,177 B2 | | 8/2016 | Thangadorai et al. |
| 9,603,868 B1 | | 3/2017 | Kennedy et al. |
| 9,623,142 B2 | | 4/2017 | Jonn et al. |
| 9,782,433 B2 | | 10/2017 | Kennedy et al. |
| 9,901,658 B2 | | 2/2018 | Kennedy et al. |
| 2002/0037310 A1 | | 3/2002 | Jonn et al. |
| 2003/0015557 A1 | * | 1/2003 | D'Alessio ........ A61B 17/00491 |
| | | | 222/570 |
| 2006/0247568 A1 | | 11/2006 | Stenton |
| 2006/0282035 A1 | | 12/2006 | Battisti et al. |
| 2007/0147947 A1 | | 6/2007 | Stenton et al. |
| 2008/0071208 A1 | | 3/2008 | Voegele et al. |
| 2008/0072432 A1 | | 3/2008 | Teys et al. |
| 2008/0105580 A1 | | 5/2008 | Nentwick et al. |
| 2008/0167681 A1 | | 7/2008 | Stenton |
| 2008/0177246 A1 | | 7/2008 | Sullivan et al. |
| 2011/0137339 A1 | | 6/2011 | Stenton |
| 2013/0131720 A1 | | 5/2013 | Quintero et al. |
| 2014/0094847 A1 | * | 4/2014 | Mach ................. A61B 17/0057 |
| | | | 606/214 |
| 2015/0328357 A1 | | 11/2015 | Kennedy |
| 2016/0015373 A1 | | 1/2016 | Russo et al. |
| 2018/0187142 A1 | * | 7/2018 | Truong ................... C12Q 1/22 |
| 2018/0264507 A1 | | 9/2018 | Hiemer et al. |
| 2019/0099170 A1 | | 4/2019 | Russo |

OTHER PUBLICATIONS

Denshine, Dental Intraligamental Syringe Anesthetic Pen Style 1.8mL Instruments webpage capture May 3, 2022, https://web.archive.org/web/20220520114035/https://denshinedental.com/products/dental-syringe-anesthetic-pen-style-189311.

* cited by examiner

ADHESIVE APPLICATOR INCLUDING NOVEL APPLICATOR TIP

FIELD OF THE INVENTION

This invention relates to applicators for dispensing and/or applying a fluid material on a surface, in particular a reactive fluid such as an adhesive material, for example, a polymerizable monomer compound such as a cyanoacrylate composition which is used to adhere or hold together separate elements. This applicator is particularly suitable for medical use as a soft tissue, or more precisely a topical adhesive, but could also be used for other applications requiring precise and easy use including sealants, coatings, lubricants, or paints.

BACKGROUND OF THE INVENTION

Numerous applications require precise application of a fluid to a surface. These fluids maybe reactive or non-reactive in nature. Non-reactive fluids include lubricants, ointments, creams, and so forth, where reactive fluids include sealants, paints, and adhesives, among others. Monomer and polymer adhesives are used in household, industrial and medical applications including for example surgery and dentistry. Popular adhesives include the cyanoacrylate monomers and polymers. This popularity is due to the speed with which they cure, the strength of the resulting bond formed, and their relative ease of use. These characteristics have made cyanoacrylate adhesives a favorite choice for bonding plastics, rubbers, glass, metals, wood, and biological tissues.

Medical applications of these reactive fluid adhesives and sealants include use in topical applications as an alternate or in addition to surgical sutures and staples in wound closure as well as for closing, covering and protecting incisions and wounds such as lacerations, abrasions, burns, stomatitis, sores, and other open surface wounds. Other applications call for prevention of flow in or through vessels, such as occlusive devices. When such an adhesive or sealant is applied, it is usually applied in monomeric form which in some instances requires an initiator and/or accelerator that contacts the monomeric form, and the resultant polymerization gives rise to an adhesive bond with the tissue substrate.

However, the requirements of sterilization, handy manipulation of the adhesive to consistently apply the adhesive in its monomeric form, and the rapid polymerization rate of the monomers have added greatly to the difficulty in designing effective and commercially viable applicators. Applicator design issues include consistent and precise, repeatable placement of the adhesive fluid, proper polymerization timing and rate, ease in applicator use, stability issues during storage, and sterilization properties of both the monomer and the applicator which is of paramount importance for medical use. The applicator design has also to account for viscosity consideration and loss of the adhesive which tends to be supplied and applied in relatively small quantities, (i.e., from 0.3 to 2 ml+/−0/05 ml).

Industrial production of any reactive fluid, and especially monomeric adhesive compositions has had to balance bond strength properties with shelf-life considerations, particularly with respect to cyanoacrylate monomers due to rapid cure rates, high reactivity, and low stability which cause them to be prone to premature polymerization.

The shelf-life of these adhesives is primarily related to stability (i.e., constancy of compositional nature), uncured physical properties, rate of cure of the adhesive, as well as final cured properties of the composition. For example, the shelf-life of a monomeric cyanoacrylate composition may be measured as a function of the amount of time the composition can be stored before unacceptable levels of polymerization occurs, as typically measured by changes in viscosity, color, purity, water content, and setting time. Medical uses include the additional complication of the requirement of sterilization of the entire finished system including the applicator and the adhesive; this complication also affects design considerations for the applicator and dispensing unit.

SUMMARY OF THE INVENTION

The present invention addresses the above needs by providing applicators that permit economical, ergonomic, convenient, and efficient use of appropriate quantities of fluid compositions, especially for reactive fluids and particularly medical adhesives. The invention is particularly favorable for use with adhesive that is contained in a breakable ampoule or rupturable or puncturable container and provides for advantages in an improved means for breaking the ampoule. Typically, breakable ampoules may comprise a brittle, inert material, such as glass at a thickness which will rupture, shatter or otherwise open with an appropriate amount of force. Other materials, such as foil or plastic, can be used, and having various "breaking" characteristics including any low impact opening. Such breakage, rupture, puncture or other similar such action or actions results in the loss of containment of the fluid, reactive fluid or adhesive from said container, ampule or other part containing the fluid.

These improvements include a lower breaking force and preferential breaking of the ampoule at the distal end to allow for more efficient use of the adhesive. In addition, the invention provides for the isolation of the shards in a rigid chamber to reduce both the chance, and the perception of risk of, user injury from a glass shard. In addition, the invention has an improved method of delivery of the adhesive. The isolation of the glass shards allows for a thinner wall and more deformable elements. In certain embodiments, a lever mechanism provides both a mechanical advantage, and an ergonometric pen-shaped form which can be cradled in the crook of the thumb and activated by one of several user fingers. Finally, the design allows for the adhesive flow to be controlled with greater precision through the lever or button, and further with the provision of an applicator tip that is specifically designed to permit the smooth flow and application of a line of adhesive of varying width.

The present applicator is designed to provide acceptable sterilization, stability, and shelf-life to the adhesive composition, as well as to the applicator itself.

In the preferred embodiments of the invention, the adhesive is provided as a monomer or pre-polymer in a frangible container, such as an ampoule, which is cracked to release the adhesive into a cavity which is in communication with plug that is loaded with an appropriate level of initiator. The adhesive is pumped through the initiator plug and applied to the substrate where it rapidly undergoes polymerization to cause adhesion.

In alternate embodiments it is also possible to use other methods to introduce an initiator to the monomer; for example, it may be coated on a surface of the applicator, or be introduced to a substrate binder or reinforcement, such as a mesh layer, or otherwise incorporated into a different portion of the applicator. U.S. Pat. No. 9,623,142 teaches an example of such a method. In particular, this reference relates to a method of bonding tissue comprising: placing a flexible material over a tissue substrate, wherein a polymerization initiator or rate modifier is immobilized in or on said flexible material; a polymerizable adhesive composition is applied over and fully covering the flexible material; the polymerizable adhesive composition is allowed to permeate into and under the flexible material and polymerize to form a composite structure bonded to the tissue substrate; and a polymerizable adhesive composition is applied to the tissue substrate prior to placing the flexible material over the tissue substrate.

In a further embodiment, the adhesive is released into a first compartment upon breaking of an ampoule which contains it, and then is pumped into a second compartment which allows the user to squeeze the walls of the second compartment between thumb and forefinger to direct the application of the adhesive onto the tissue or mesh substrate. In this case, the applicator and/or dispenser may also include a porous barrier separating first and second compartments, for example, to keep the polymerization initiator or accelerator separated from the adhesive material prior to use. The barrier acts as a sieve placed to prevent glass shards from migrating into the deformable chamber. This aspect of the invention has multiple advantages: 1) it minimizes adhesive "hold-up" on shards, and 2) it reduces the risk of shard penetration through deformable chamber wall which could stab the user, and 3) this allows the use of a thinner reservoir wall (since there is less threat of the shards), which is more easily deformed for more a comfortable and better controlled application of adhesive.

In particular, this invention is directed to an applicator for dispensing and/or applying an adhesive material, comprising: a first body portion including a cavity for a frangible ampoule and an actuator which is movable relative to the cavity and a piercing or breaking member which is within the cavity wherein movement of the actuator relative to the cavity moves the ampoule into the piercing or breaking member in the cavity so as to break the ampoule and release the contents or in one embodiment includes a spring loaded breaking member, such as a wire member, that snaps the ampoule when it strikes it.

In various embodiments, the applicator/dispenser further comprises a breakable container of adhesive material at least partially disposed within the applicator cavity or open space, wherein movement of the actuator causes the ampoule to contact or move the piercing or breaking member to rupture it. This also allows the user to control the flow of the adhesive. Thus, the invention uses a single mechanism to open the adhesive container and to control the flow of the adhesive.

Advantageously in one embodiment, the actuator is on a lever linkage which provides mechanical advantage to the movement of the ampoule, facilitating easier breaking of the ampoule. Movement of the actuator causes the distal end of the ampoule to encounter a cracking wedge also at the distal end of the cavity, shattering the ampoule and allowing adhesive monomer to flow through a porous filter out an applicator tip. The ampoule cavity is sealed at its proximal end by a reciprocating piston member formed as a ram cap member which holds the ampoule and is coupled to the linkage, and wherein the movement provides hydraulic pressure in the cavity to control flow of adhesive from the cavity. With the lever linkage design, the lever is provided as a handle which pivots about a hinge axis transverse to the long axis of the housing and has a counter spring member which acts to bias the lever back to the "starting" position. The lever linkage forces the ampoule down the path that encounters the cracking wedge, and also applies a fluid pressure to the fluid that is released into the cavity of the applicator to flow through the applicator tip and out of the applicator. When the lever spring acts in contravention to this force, the flow of the adhesive is stopped, and can even cause the adhesive to be drawn back into the nozzle of the container. In a further embodiment, the distal end of the ampoule is broken when a spring-loaded wire member is released and snaps into the end of the ampoule with sufficient force to break it.

The invention provides a slim elongate applicator which has a balanced fit in the hand of a user with a terminal applicator tip aligned along the long axis of the applicator. Thus, the applicator fits, much like a pen, on the medial surface of the hand balanced on the forefinger and in the crook of the thumb, to dispense the adhesive from the distal end through the terminal applicator tip. The uncured adhesive formulation is contained in in a breakable ampoule which helps to solve issues relating to premature cure. An additional benefit of the invention is that the user can hold the pen in various configurations in the clinical settings and choose which finger presses the lever and where the finger contacts the lever. The pivot point is at one end of the applicator with a relatively long lever to give good mechanical advantage at the distal end of the applicator. There is even the option of holding the applicator like grip exercisers.

In several embodiments provided, the applicator includes various mechanisms to apply a force in the direction of the long axis of the applicator to the ampoule, which encounters a cam and opposing cracking member designed to maintain and center the direction of travel of the ampoule during breakage and so that it breaks at the distal end and so that it does not hang up off axis in the cavity. This reduces the amount of waste of the adhesive since it is more readily available to an opening in the applicator which is in fluid communication with an applicator tip.

In one embodiment, the user simply pushes on a button which directs the ampoule along the long axis of the applicator, while another embodiment uses a spring-loaded wire cracker to snap the ampoule, and a third embodiment advantageously uses a lever linkage which presses on a pneumatically sealed piston head that surrounds the ampoule. The lever embodiment provides a mechanical advantage to reduce the strength needed to break the ampoule and stops the flow of adhesive when the handle lever is released.

The ampoule is advantageously held in a fluid tight cavity within the applicator that is in communication at the distal end with a filter/initiator member. This member is a porous disk that filters glass shards from the broken ampoule while allowing the adhesive monomer to pass into an opening in an applicator tip. In addition, the filter/initiator member holds an appropriate level of initiator to initiate the cure of the monomer prior to application on the substrate. An actuator includes a sealing member, such as an O-ring or flange or wiper modified O-ring that seals the ampoule cavity to cause the movement of the actuator to affect the pressure of the cavity.

In one embodiment, the ampoule is placed in a housing which includes the sealing member and forms a closed system of the cavity. In this embodiment, a linkage is acted on by a lever to translate the ampoule and housing along the long axis of the applicator in the cavity and to press the distal end of the ampoule into the wedge cam and cracking member. In this embodiment, the lever is also subjected to a spring force from an integral spring arm or leaf spring in the opposite direction so that the lever is resilient to being depressed into the dispensing position, and when the user releases the downward and inward pressure, the adhesive stops flowing out, or may even be slightly drawn back into the applicator.

The applicator preferably includes a novel adhesive applicator tip that is comprised of a flexible material inert (or substantially non-reactive and preferably non-reactive on the timeframe of fluid dispensing or adhesive polymerization) to the adhesive and having a terminal portion that ends in a slant or chisel edge including a recess, such as an arcuate concavity. The recess includes a central slot in the long direction bounded on at least the longer edge of the applicator tip by a tip or nose that acts to block the adhesive bead being laid down from spreading during application. Optionally, the tip end may include extended tips on each end of the exit slot. As the adhesive is drawn from the adhesive cavity through a porous filter that includes an initiator, it is laid unto the substrate (i.e., the patient's skin) in a bead. As the initiator is first introduced onto the substrate, it is relatively fluid, but becomes more viscous with the passage of time as it cures. The surface tension between the adhesive and the substrate causes the bead to wet the substrate and as the applicator is drawn over the substrate, the bead is drawn from the tip feed recess unto the substrate and the applicator tip nose acts either like a doctor blade or a pen nib to block or draw the adhesive over the substrate to form the desired configuration, which can be a wide or narrow line or adhesive.

Advantageously, the handle also includes markings to allow it to be used as a ruler to measure or estimate the length of an incision as can be required for regulatory purposes.

BRIEF DESCRIPTION OF THE DRAWINGS

Exemplary embodiments of this invention are described in detail below, with reference to the attached drawing figures, in which.

DETAILED DESCRIPTION OF THE INVENTION

An applicator 100, (200, 300, 400, 500), is provided that facilitates easy and comfortable application of a desired quantity of polymerizable adhesive material, in particular in a pen-like housing 102, (202, 302, 402, 502). In embodiments, an amount of polymerizable adhesive material 104 is prepackaged in the applicator/dispenser in a frangible ampoule 106 that is broken upon activation of the applicator/dispenser. The frangible ampoule is preferably a glass, metal, or silicon material that is shaped like a lozenge which is illustrated as cylindrical with rounded end members which may or may not be symmetrical and have the same shape. The ampoule may provide stability and/or shelf-life for a polymerizable adhesive material.

Figure 1:
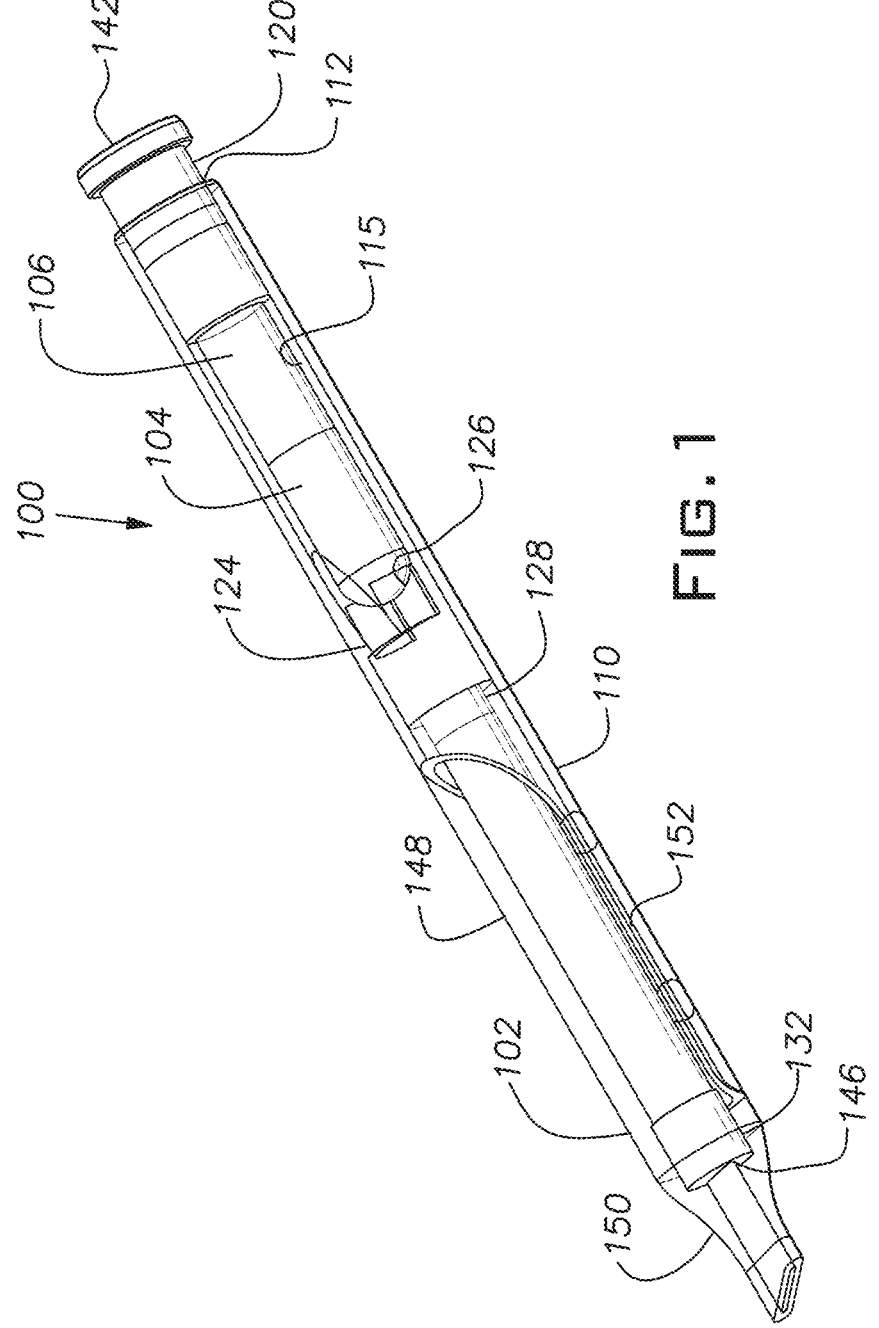
FIG. 1 is a side view of a first embodiment of this invention.
Figures 2A, 2B:
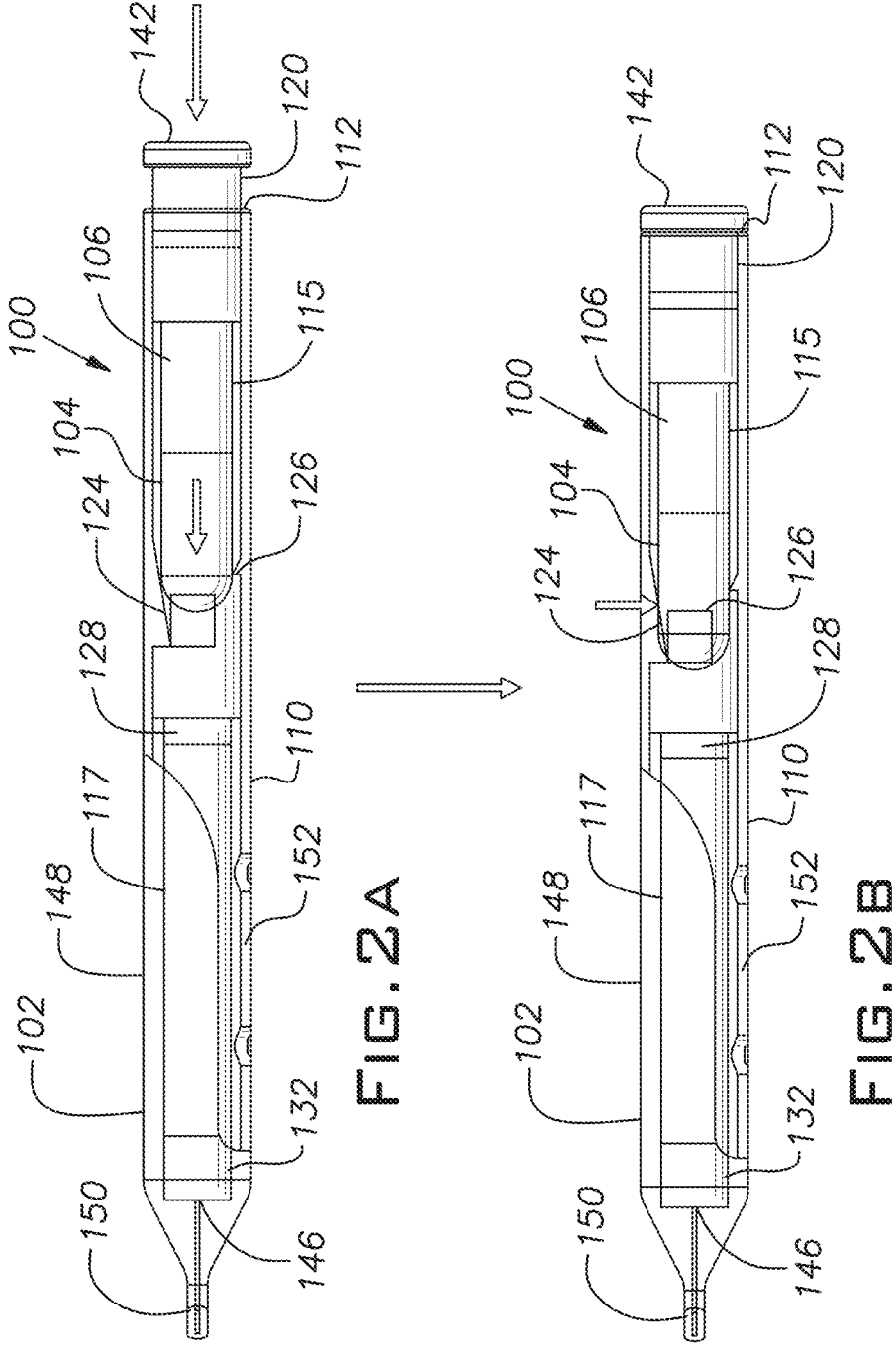
FIG. 2(*a*) and FIG. 2(*b*) are side views of the first embodiment shown in FIG. 1 and illustrating activation of the applicator.
Figures 4A, 4B:
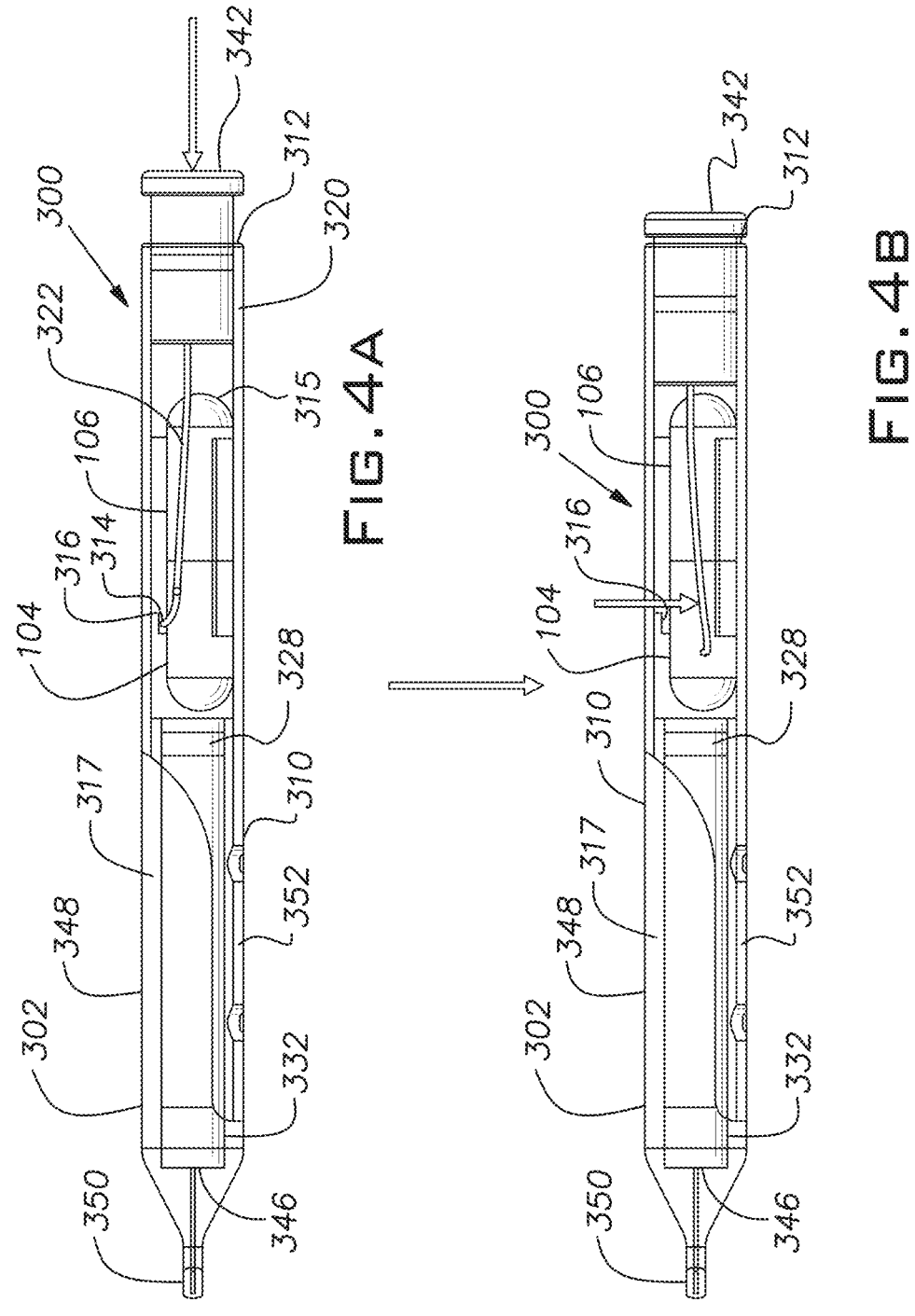
FIG. 4(*a*) and FIG. 4(*b*) are side views of a third embodiment and illustrating activation of the applicator.
Figure 5:
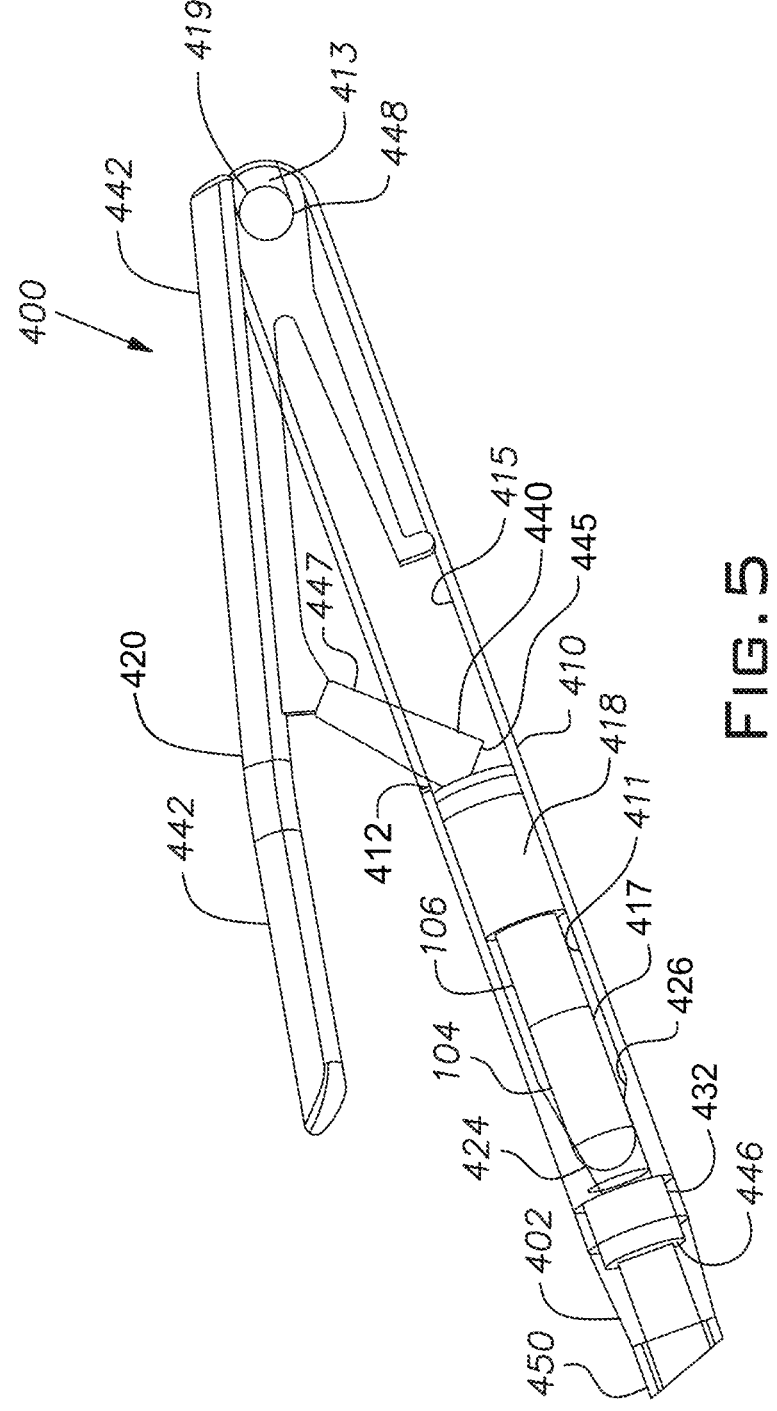
FIG. 5 is a perspective view of a fourth embodiment of this invention.
Figure 6:
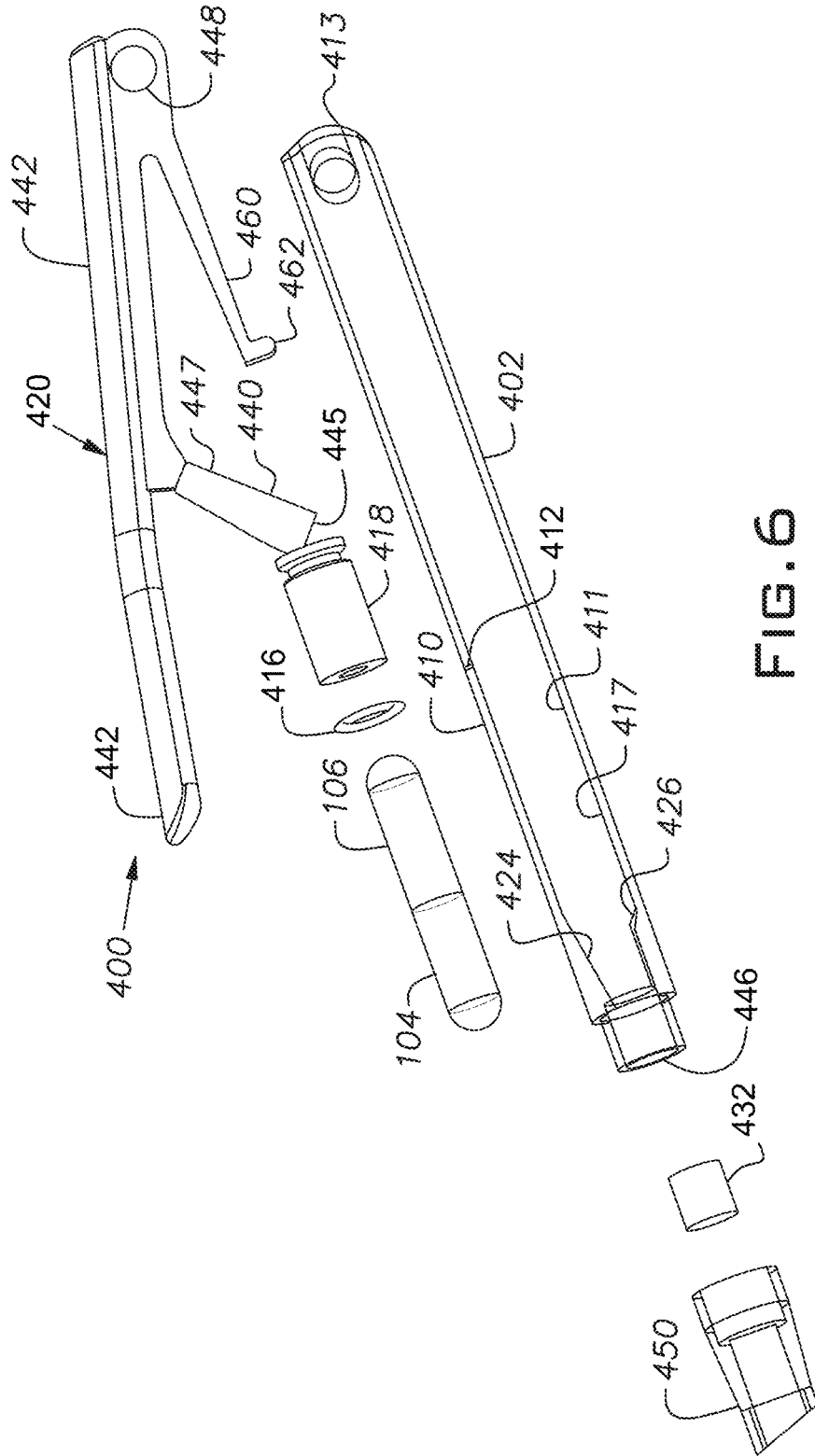
FIG. 6 is an exploded view of the embodiment of FIG. 5 illustrating the components.
Figure 7:
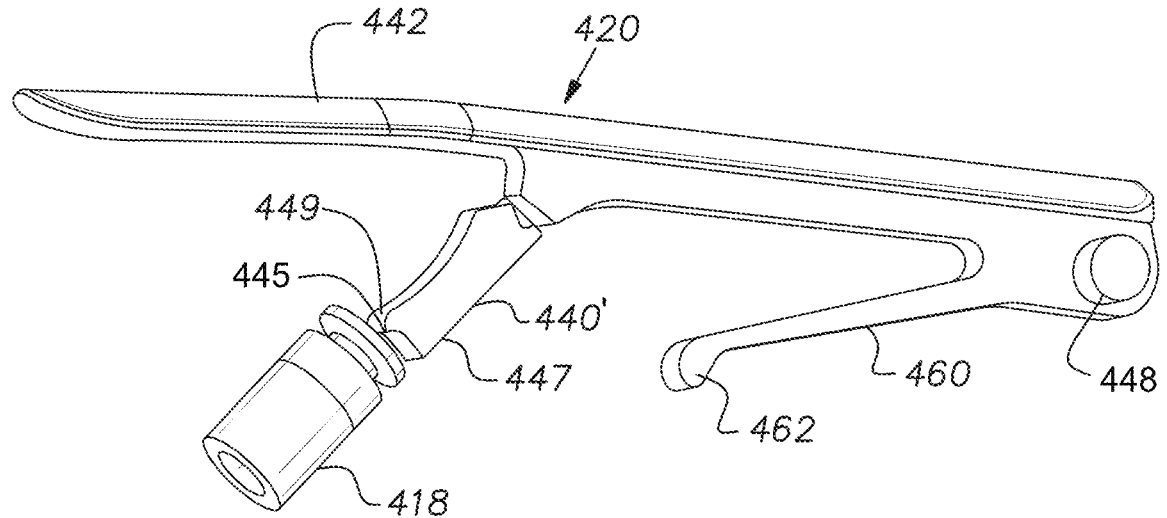
FIG. 7 is a side view of a further embodiment of the lever linkage of the embodiment of the applicator of FIG. 5, and including an integral pivoting handle, a first linage arm, a spring arm and a separate ampoule ram cap member.
Figures 8, 9, 10, 11, 12:
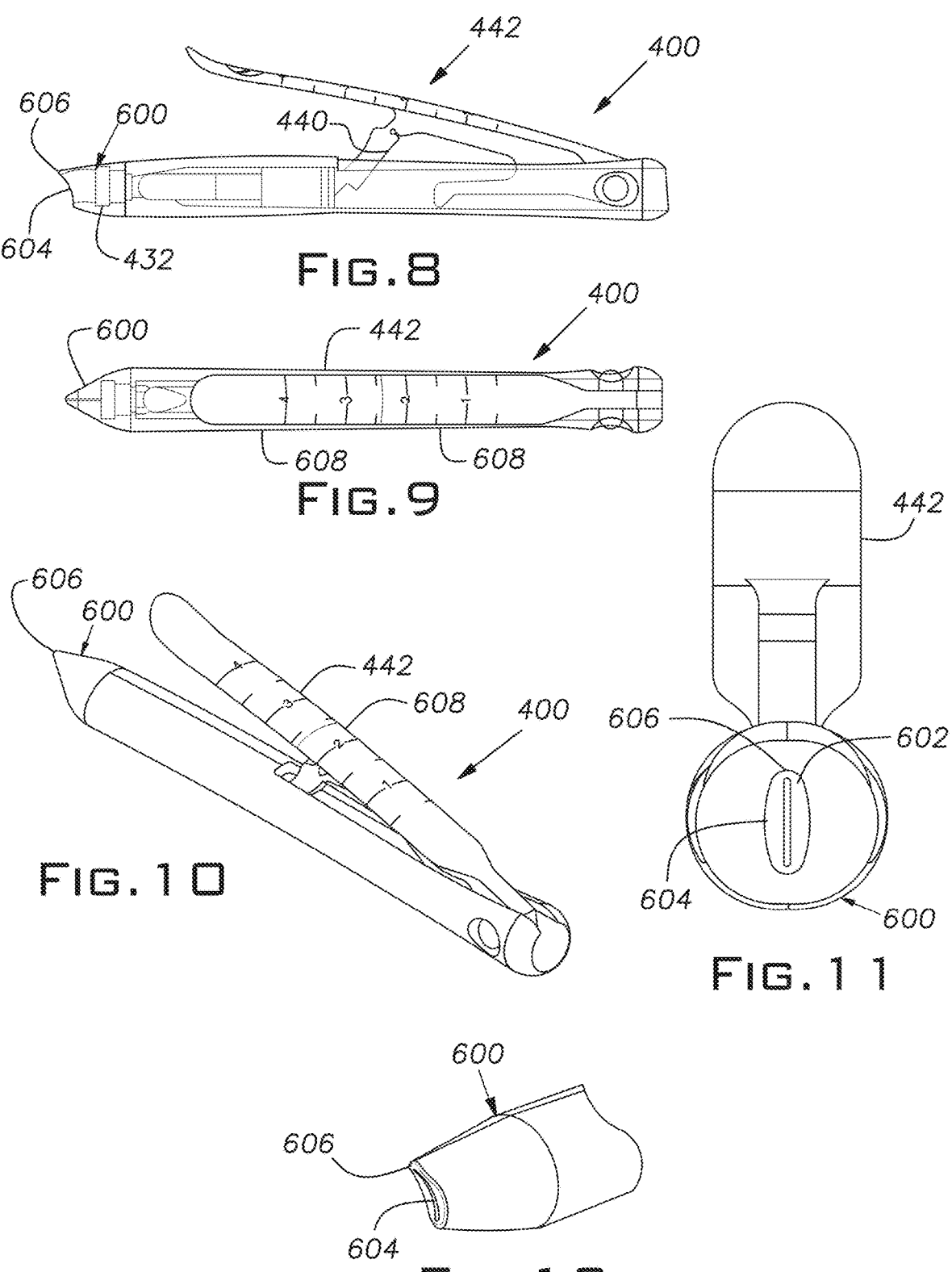
FIG. 8 is a side cross sectional view of the fourth embodiment of the applicator including the novel applicator tip.
FIG. 9 is a side view of the fourth embodiment of the invention showing the ruler marked handle.
FIG. 10 is a perspective view of the fourth embodiment of this invention.
FIG. 11 is a distal end view of the embodiment of FIG. 8 illustrating the applicator tip.
FIG. 12 is an end side view of the applicator tip of the applicator of FIG. 8.
Figure 13:
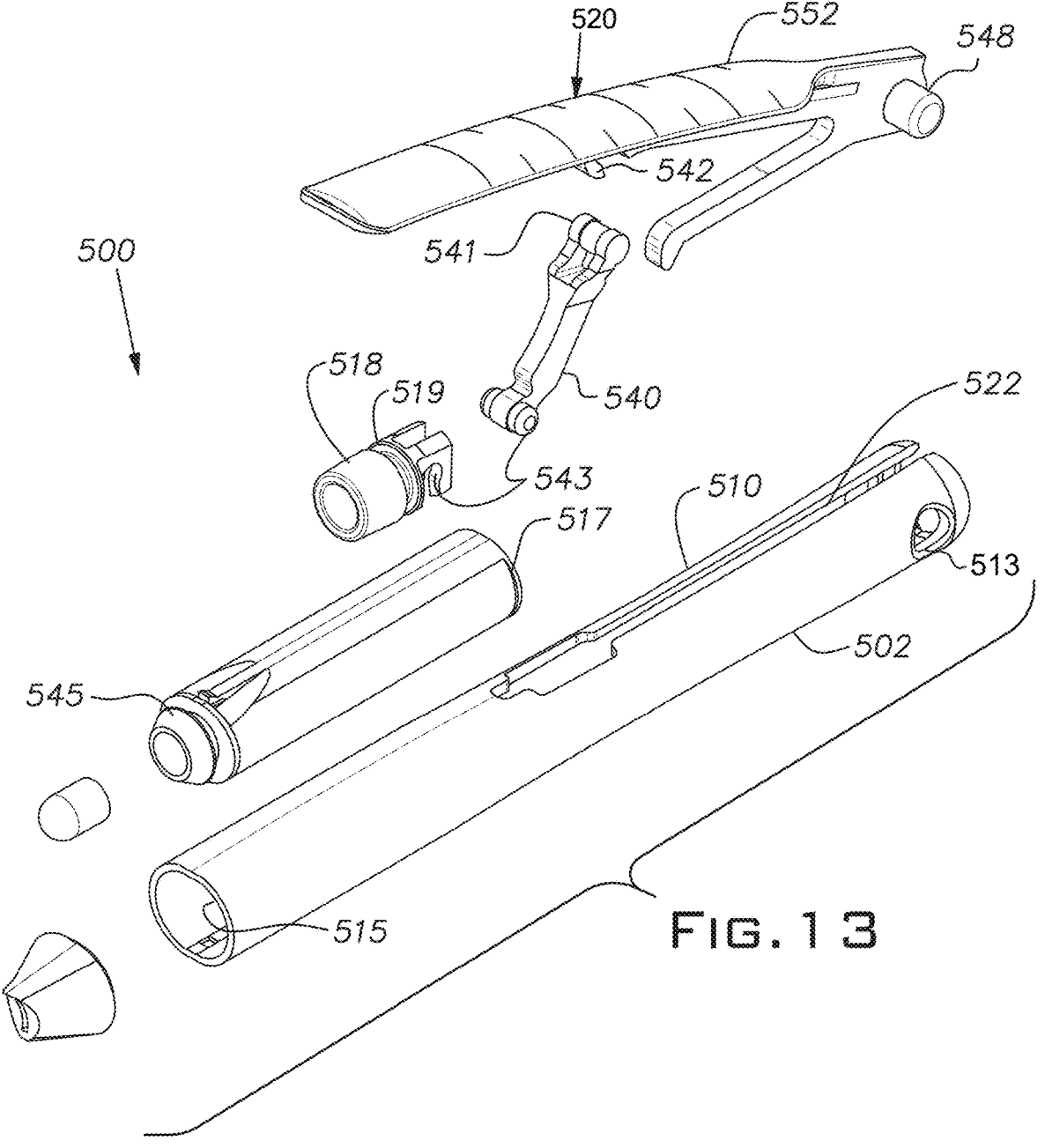
FIG. 13 is a front side view of an exploded assembly in accordance with a fifth embodiment of the invention.
Figures 14, 15, 16, 17, 18:
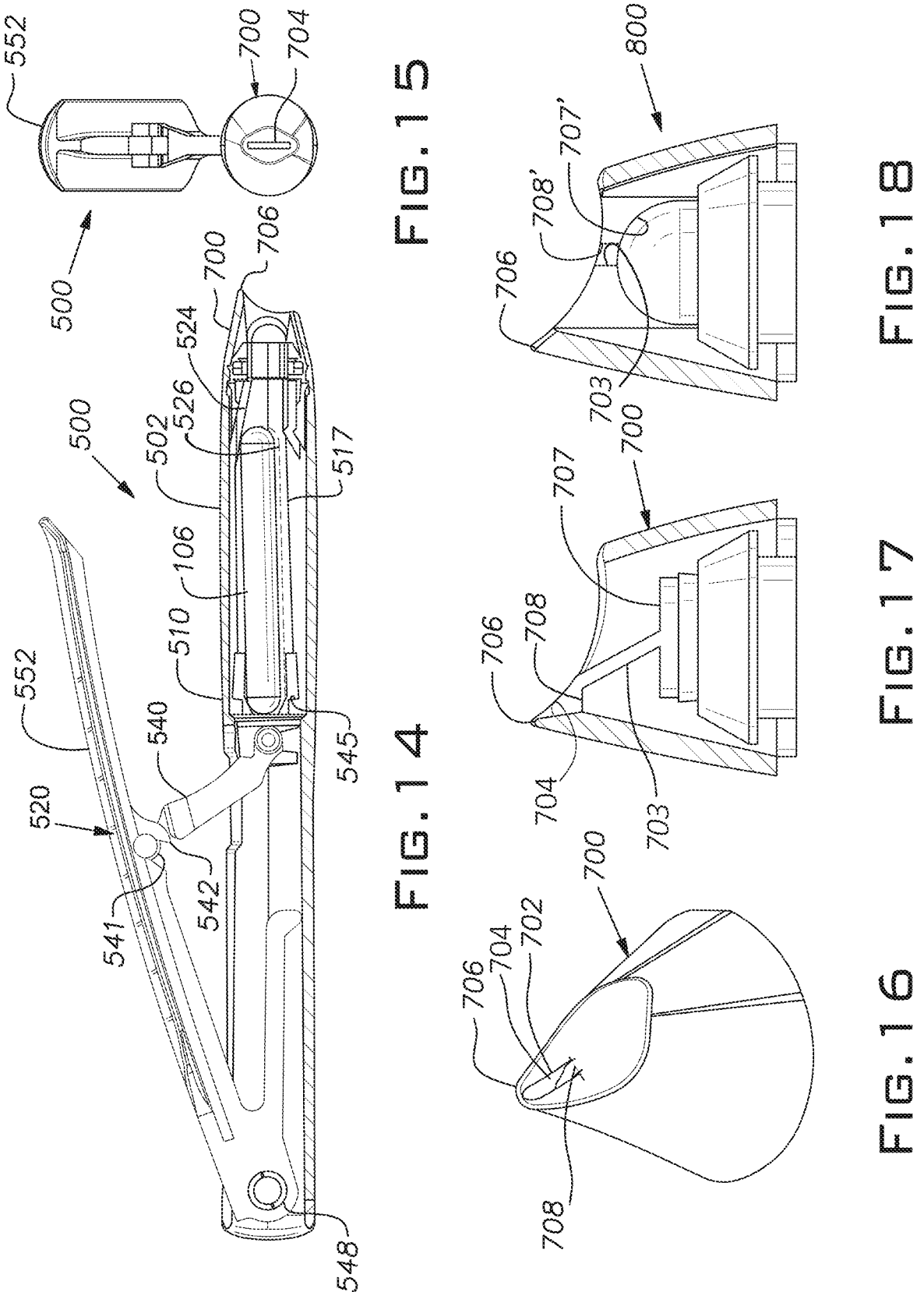
FIG. 14 is a side cross-section of the applicator assembly of FIG. 13.
FIG. 15 is a front end view of the applicator assembly of FIG. 13.
FIG. 16 is a top side view of a further embodiment of the applicator tip in accordance with the invention.
FIG. 17 is a side cross section of the applicator tip of FIG. 16.
FIG. 18 is a cross-section of an alternative embodiment of the applicator tip shown in FIG. 16.

FIGS. 1, 2(*a*) and 2(*b*) illustrate a first embodiment of the applicator 100 of this invention, FIGS. 3(*a*) and (*b*) illustrate a second embodiment 200, FIGS. 4(*a*) and 4*b*) illustrate a third embodiment of the applicator 300 of the invention, FIGS. 5-7 illustrate a fourth embodiment of the applicator 400 or the invention and FIGS. 13-15 illustrate a fifth and preferred embodiment of the applicator 500, while FIG. 16 illustrate versions of the applicator tip 700, 800 in accordance with the invention.

As shown in FIGS. 1,2(*a*) and 2(*b*), an applicator 100 is formed by an elongate first body portion 110 having a long axis and a push-button actuator 120 that is movable relative to the body portion in the direction of the long axis. The body member includes a first open space 115 with a breakable ampoule 106 containing a prepackaged amount of polymerizable adhesive material 104. The first open space 115 has a proximal opening 112 through which a push button portion 142 of the actuator 120 extends. The first open space has a terminal distal portion that includes a wedge member 124 and a cracking member 126 which opposes the wedge member 124. This arrangement causes the ampoule to travel along the long axis of the body portion as it encounters the cracking member and helps to ensure a smooth travel as the ampoule breaks against the cracking member. The first open space is in fluid communication with a dispensing cavity 117 and is separated by a first plug or filter member 128 that keeps pieces of the ampoule from entering the dispensing cavity 117. The push button portion 142 (which can include a coil spring for resilience) is depressed by a user to dispense the polymerizable adhesive material into the second dispensing cavity 117 which is open through a porous disk 132 that also contains an initiator to a distal opening 146. The user can dispense the adhesive from the second cavity, for example, through a detachable or replaceable tip 150 at the distal opening 146 by squeezing the soft and deformable walls 148 of the dispensing cavity to force the adhesive out of the applicator. The tip is preferably a wedge shape with a vented bevel leading edge. The vented bevel tip will clear debris from the leading edge and allow a specific width and thickness of an adhesive layer. A user's thumb and finger may be used to depress the outer walls of the dispensing cavity. The user can use a thumb to depress the button portion 142 while the applicator 100 is grasped in the hand by the body portion 110, or the user can invert the applicator and press the button portion against a hard surface, like a table. For example, a user may hold the applicator/dispenser 100 as a pen and press the push button portion 142 with an index finger or thumb. A shroud member 152 encloses at least a portion of flexible element 148 to provide a rigid surface to counteract forces applied to flexile element 148 while dispensing adhesive for purposes of stabilizing the applicator tip.

If the optionally detachable or replaceable tip 150 is not provided or used, a porous plug may form the tip of the dispenser/applicator 100. The tip 150 may be selected for a particular application and is not limited to the tapered nozzle design shown. For example, the applicator tip may be a fibrous swab, a sponge swab, a foam swab, a brush, a spatula, or the like. Any suitable tip, either known or hereafter developed, may be used with the applicators/ dispensers according to this invention.

Figures 3A, 3B:
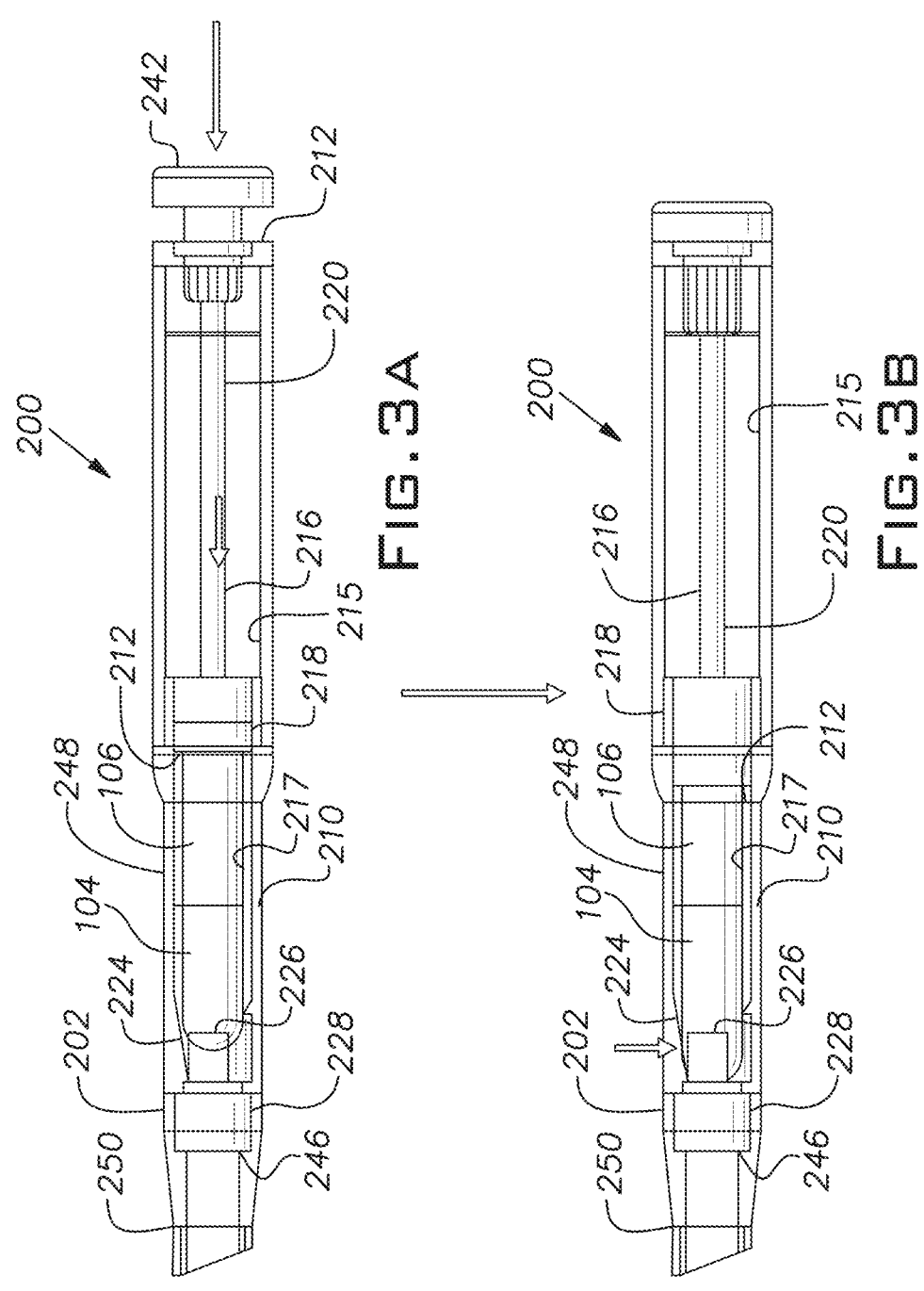
FIG. 3(*a*) and FIG. 3(*b*) are side views of a second embodiment and illustrating activation of the applicator.

As shown in FIGS. 3(a) and 3(b), an applicator 200 is again formed by an elongate first body portion 210 having a long axis and an actuator 212 that is movable relative to the body portion in the direction of the long axis. The body member includes the first open space 215 which houses a rod 216 and ram cap member 218 of the actuator 220 and a second open space 217 aligned along the long axis of the body portion 210 that contains a breakable ampoule 106 containing a prepackaged amount of polymerizable adhesive material 104. The second open space 217 has a proximal opening 212 through which a push button portion 242 of the actuator 220 extends. The second open space 217 has a terminal distal portion that includes a wedge member 224 and a cracking member 226 which opposes the wedge member 224. Again, this arrangement causes the ampoule to travel along the long axis of the body portion as it encounters the cracking member and helps to ensure a smooth travel as the ampoule breaks against the cracking member. The second open space provides a dispensing cavity and is separated from the outflow exit 246 by a filter member 228 that also includes an initiator and that keeps pieces of the ampoule from entering the exit 246. The push button portion 242 is depressed by a user to shatter the ampoule, releasing the adhesive contents into the dispensing chamber 248. The user can dispense the adhesive for example, through a detachable or replaceable tip 250 at the distal opening 246 by squeezing the soft and deformable walls of the first open space 215 to force the adhesive out of the applicator. A user's thumb and finger or palm may be used to depress the outer walls of the first open space 215. The user can use a thumb to depress the button portion 242 while the applicator 200 is grasped in the hand by the body portion 210, or as previously described, the user can invert the applicator and press the button portion 242 against a hard surface, like a table. For example, a user may hold the applicator/dispenser 200 as a pen and press the push button portion 242 with an index finger or thumb. The dispensing chamber 248 is rigid, and the ampoule glass is captured in this rigid part, which tends to be more distal than in previous embodiment to eliminate some hold-up/drainage issues. Consequently, the user's hand is somewhat proximal from the tip compared to other embodiments to assure greater visualization of the target application site.

As shown in the embodiment illustrated in FIGS. 4(a) and 4(b), an applicator 300 is again formed by an elongate body portion 310 having a long axis and an actuator 320 that is movable relative to the body portion in the direction of the long axis. The body member 310 includes a first open space 315 with a breakable ampoule 106 containing a prepackaged amount of polymerizable adhesive material 104. The first open space 315 has a proximal opening 312 through which a push button portion 342 of the actuator 320 extends. In this embodiment the actuator 320 includes a wire member 322 which extends into the first open space 315. The proximal end of the wire member 322 is captured in a press button 342 which is captured in the proximal opening 312 of the body member. The distal end of the wire member has a cross wire 314 that is held in a cocked position in a retention member or hook 316 in the interior wall of the open space 315. When the press button 342 is depressed to move the actuator along the long axis of the body member, the cross wire is disengaged from the retention member or hook 316 and allowed to spring back to a biased position onto the ampoule where it breaks the ampoule 106. As in the first embodiment, the applicator 300 includes a second open space 317 which is separated from the first open space by a porous plug 328 that filters shards of the ampoule from the dispensing cavity of the second space. The push button portion 342 is depressed by a user to dispense the polymerizable adhesive material into the second dispensing cavity 317 which is open through a porous disk 328 that also contains an initiator to a distal opening 346. The user can dispense the adhesive from the second cavity, for example, through a detachable or replaceable tip 350 at the distal opening 346 by squeezing the soft and deformable walls 348 of the dispensing cavity against a more rigid shroud 352 to force the adhesive out of the applicator. A user's thumb and finger may be used to depress the outer walls of the dispensing cavity, again with a rigid opposing element to provide stability during expression of the adhesive.

A fourth and preferred embodiment is shown in FIGS. 5-7, Here, an applicator 400 is again formed by an elongate body portion 410 having a long axis and an actuator 420 having a long handle 442 that has a boss 448 captured in a recess 412 in the body so that it pivots, causing a lever linkage 440 to apply a force relative to the body portion in the direction of the long axis. The body member includes an open space 415 which houses the lever linkage 440 and separate ram cap member 418 of the actuator 420. The body member has a second open space 417 defined on the distal side of the ram cap member 418 within the main cavity 411 of the body member. The first and second spaces 415, 417 are aligned along the long axis of the body portion 410. The second open space 417 contains a breakable glass ampoule 106 containing a prepackaged amount of polymerizable adhesive material 104. The main cavity 411 has a proximal slot opening 422 through which a lever linkage 440 of the actuator 420 extends.

The handle 442 of the actuator 420 includes a boss 448 having an edge 419 which is received in a recess 413 in the body member 402. This allows the handle member 442 to pivot from an open position toward the exterior wall of the body member 402 simply by closing one or more finger(s) while balancing the applicator in the hand like a pen. As the handle member 442 pivots, the linkage 440 moves through a slot in the body wall and applies a force with a component along the long axis of the body member. The linkage 440 has an arm 447 with and end 448 (and in FIG. 7, the end 448' of the lever linkage includes a finger 449) that is captured in a depression in the ram cap member 418 to transfer the force from the lever linkage 440 through the ram cap member 418 to the ampoule and to press the distal end of the ampoule against the cam 424 and into the cracking member 426. Again, this arrangement causes the ampoule to travel along the long axis of the body portion as it encounters the cracking member 426 and helps to ensure a smooth travel as the ampoule breaks against the cracking member 426. FIG. 7 advantageously illustrates an embodiment where the entire depicted element is injection molded as one part. The linkages on both ends of 440' are "living hinges", which can be made as one piece of plastic, or interacting component parts. It is important to the proper functioning of the design that the cam 424 that biases the ampoule down onto the cracking member 426 is distal to the cracking member. This is needed to minimize breaking force, as the ampoule is very strong at the extreme ends. It is therefore an advantage to have the cracking member fracture the ampoule proximal to the distal end of the ampoule. This also provides leverage to amplify the downward force on the cracking member.

The ram cap member 418 includes an O-ring 419 or concentric flange that forms a tight sliding or sealing engagement against the interior wall of the body member. This tight engagement creates a region of increased pressure within the second open space 417 of the body cavity 411 when the lever 442 is depressed, thereby providing pneumatic pressure to drive adhesive 104 from the applicator. It should be noted that the ampoule resides deeply in a counterbore in the ram cap member 418. This maintains the ampoule coaxial to the applicator as the ram cap member pushes it forward. Without this feature, the ampoule could misalign in the applicator as it encounters the surface of the cam 424 and cracking member 426, causing inconsistent breakage of the ampoule. As it functions, only the distal end of the ampoule shatters, leaving a proximal 80% of it intact. This results in less hold-up of adhesive on shard surfaces.

The second open space 417 provides a dispensing cavity and is separated from the outflow exit 446 by a filter member 432 that also optionally includes an initiator and an exit, such as pores, that keeps pieces of the ampoule from entering the terminal tip 450. The actuator assembly has an integral spring arm 460 with a distal rider 462 which presses against the interior wall of the body cavity 411. This spring member 460 opposes pivoting pressure of the handle member 442 toward the body 402 such that when the user releases the handle member 442, the handle member 442 tends to pivot away from the body, which in turn stops the pressure on the ram cap member and stops the flow of or even withdraws the adhesive. This in turn creates an area of decreased pressure in the second open space 417 which subsequently at least partially equalizes in pressure with the surrounding atmosphere via inflow of air through the outflow exit 446. This re-entry of air into the second open space with the handle member 442 in the outward position away from the body 402 enables re-creation of increased pressure within the second open space via re-depression of the handle member 442 and subsequent continued expression of the fluid through the outflow exit 446. Thus, the user, by repeated depression or release of the lever handle member 442 may stop and re-start flow of the fluid out the exit 446 an arbitrary number of repetitions, enabling intermittent and repeated flow without necessitating any repositioning of fingers or hand.

A third embodiment of the invention is shown in FIGS. 8-12, which includes a novel applicator tip. Advantageously, as is shown in FIGS. 8-11, a delivery tip 600 is provided that has a modified chisel shape having a slot shaped outlet 602. The slot 602 is approximately 0.5 mm (+/−50% and preferably 25%) with a length of 5-10 mm (+/−50% and preferably 25%). The tip 600 joins the cylindrical body of the applicator with the chisel shaped end so that it tapers downward and inward. The end of the tip forms a recess 604 that is preferably arcuate, and which has a bump, tip, nose or nib 606 on at least one side to shoulder a pool of adhesive held in the recess. The recess forms a well for the accumulation of the adhesive where the nib can be used to control the application of the pooled fluid prior to cure. The tip is preferably made of a soft, flexible material, such as a material having a Shore A value of 55 A or softer, preferably, 40+/−10, or 5 on the shore A scale.

The applicator tip can further include a porous plug 432 that may include an initiator and which can either be downstream or upstream of the communicating chamber which receives the fluid after the ampoule is broken, but the downstream version having the porous plug immediately terminal the communicating chamber provides an advantage for more economic use of the adhesive since the outlet is less likely to become clogged with cured adhesive and more of the adhesive should be available for use.

This version of the applicator further illustrates a handle member 442' which includes markings or indicia 608, for example inch or centimeter markings, which allow the user to place the applicator alongside an incision to estimate a length for regulatory purposes.

A fifth preferred embodiment is shown in FIGS. 13-15. Here, an applicator 500 is again formed by a pen-like elongate body portion 510 having a long axis and an actuator 520 having a long marked handle 552 that has a boss 548 captured in a recess 512 in the body so that it pivots, causing a lever linkage 540 having a pin portion of a knuckle 541 held in a hook 542 to allow the handle to pivot to apply a force relative to the body portion in the direction of the long axis. The body member includes an open space 515 which houses the lever linkage 540 and separate ram cap member 518 of the actuator 520. In this embodiment, the body member also holds a sleeve 517 that holds and directs the adhesive ampoule 106 containing a prepackaged amount of polymerizable adhesive material. The open space of the body member 515 has a proximal slot opening 522 through which a lever linkage 540 of the actuator 520 extends.

The handle 542 of the actuator 520 operates in a similar manner to the previously described embodiment except that the lever linkage 540 is an assembly that includes the ram member 518 which is also hooked to a lower knuckle 543 of the ram member to act as a piston within the sleeve 517. Again, this arrangement causes the ampoule to travel along the long axis of the body portion as it encounters the cracking member 526 and helps to ensure a smooth travel as the ampoule breaks against the cracking member 526. It is important to the proper functioning of the design that the cam 524 that biases the ampoule down onto the cracking member 526 is distal to the cracking member. This is needed to minimize breaking force, as the ampoule is very strong at the extreme ends. It is therefore an advantage to have the cracking member fracture the ampoule proximal to the distal end of the ampoule. This also provides leverage to amplify the downward force on the cracking member. In this embodiment, the sleeve end cap 545 holds the ampoule at angle relative to the long axis of the body portion long axis as is shown in FIG. 14. This causes the ampoule to encounter the cam 524.

The ram cap member 518 again includes an O-ring 519 or concentric flange that forms a tight sliding or sealing engagement against the interior wall of the body member. This tight engagement creates a region of increased pressure within the sleeve 517 within the body cavity 515 when the handle 542 is depressed, thereby providing pneumatic pressure to drive adhesive from the applicator. It should be noted that the ampoule resides deeply in a counterbore in the ram cap member 518

Aa additional embodiment of the novel applicator tip of the invention is shown in FIGS. 16-18. Advantageously, as is shown in FIGS. 16-18, a delivery tip 700 is provided that has a modified chisel shape having a slot shaped outlet 702. The slot 702 is approximately 0.5 mm (+/−50% and preferably 25%) with a length of 5-10 mm (+/−50% and preferably 25%). The tip 700 joins the cylindrical body of the applicator with the chisel shaped end so that it tapers downward and inward. The end of the tip forms a recess 704 that is preferably arcuate, and which has a bump, tip, nose or nib 706 on at least one side to shoulder a pool of adhesive held in the recess. The tip can include a well 707, 707' which is fed through a tunnel 703 into a exit opening 708, 708'

A frangible or rupturable ampoule containing an amount of polymerizable adhesive is disposed in the applicator and the frangible ampoule may be made of any suitable material such as glass, especially borosilicate glass, ceramics, polymers, especially polyolefins including cyclic olefin copolymers, metals, especially aluminum, tin as well as laminates and composites thereof. Alternatively, the adhesive may be contained in a sealed cavity within the body of the applicator where the actuator breaks or ruptures the sealing material so as to allow the exit of the adhesive material.

In addition to a polymerization initiator or rate modifier, the tip may include a medicament, an anesthetic and/or other material to be applied.

The applicators/dispensers of this invention may be used to apply the reactive or polymerizable adhesive composition to a variety of substrates for the purposes of protecting, sealing, and bonding surfaces together. Suitable substrates include, but are not limited to, metals, plastics, rubbers, wood, ceramics, fabrics, cement, paper, living tissue and the like. For example, a polymerizable and/or cross-linkable material may be useful as tissue adhesives, sealants for preventing bleeding or for covering open wounds, systems for delivery of therapeutic or other bioactive agents, and other biomedical applications. They find uses in, for example, closing surgically incised or traumatically lacerated tissues; setting fractured bone structures; retarding blood flow from wounds; aiding repair and regrowth of living tissues; providing implantable matrixes for delivering bioactive agents; dressing burns; dressing skin or other superficial or surface wounds (such as abrasions, chaffed or raw skin, and/or stomatitis); protecting tissues prone to damage (e.g., as artificial calluses); and providing structural implants.

The adhesive material, in embodiments, is preferably a monomeric (including prepolymeric) adhesive composition. In embodiments, the monomer is a substituted cyanoacrylate. Preferred monomer compositions of this invention, and polymers formed therefrom, are useful as tissue adhesives, sealants for preventing bleeding or for covering open wounds, and in other absorbable and non-absorbable biomedical applications. They find uses in, for example, apposing surgically incised or traumatically lacerated tissues; retarding blood flow from wounds; drug delivery; dressing burns; dressing skin or other superficial or surface wounds (such as abrasions, chaffed or raw skin, and/or stomatitis); hernia repair; meniscus repair; and aiding repair and regrowth of living tissue, including obstructing or occluding flow of bodily fluids where desired, for example, in U.S. Pat. No. 9,011,486. Other preferred monomer compositions of this invention, and polymers formed therefrom, are useful in industrial and home applications, for example in bonding rubbers, plastics, wood, composites, fabrics, and other natural and synthetic materials.

The monomer (including prepolymeric) adhesive composition may include one or more polymerizable monomers. Preferred monomers that may be used in this invention are readily polymerizable, e.g., anionically polymerizable or free radical polymerizable, or polymerizable by zwitterions or ion pairs to form polymers. Such monomers include those that form polymers, that may, but do not need to be, biodegrade. Such monomers are disclosed in, for example, in U.S. Pat. No. 8,431,666, for "Injectible cyanoacrylate-functionalized polyisobutylenes"; U.S. Pat. No. 9,603,868 for "Polymer adhesives comprising a low boiling point biocompatible solvent, high molecular weight multi-arm star cyanoacrylate-telechelic polyisobutylene and 2-octyl cyanoacrylate"; U.S. Pat. No. 9,695,286 for "Rubbery polysiloxanes carrying cyanoacrylate functions and related methods for their preparation and uses therefor"; U.S. Pat. No. 9,782,433B2 for "Co-network of high and low molecular weight 3-arm star cyanoacrylate-telechelic polyisobutylene and 2-octyl cyanoacrylate"; U.S. Pat. No. 9,901,658 for "Method for the production of poly(2-octyl cyanoacrylate)-polyisobutylene co-network, and super initiators therefor"; and U.S. Patent Application No. 2015/0,328,357A1 "Wound protecting polymers" all incorporated herein as if set forth in full. Additional compositions are described in U.S. Pat. Nos. 5,328,687 and 5,928,611 to Leung et al., U.S. patent application Ser. No. 09/430,177, filed on Oct. 29, 1999, and U.S. Pat. No. 6,183,593, which are hereby incorporated in their entirety by reference herein. Preferred monomers include poly (substituted cyanoacrylate) polyalkylene monomers, such as cyanoacrylates including, but not limited to, alkyl α-cyanoacrylates having an alkyl chain length of from about 1 to about 20 carbon atoms or more, preferably from about 2 to about 12 or more preferably from about 3 to about 8 carbon atoms. Other suitable monomers include, but are not limited to, polysiloxanes, polybutylenes, and alkyl ester cyanoacrylate monomers, such as those disclosed above and further, for example, U.S. Pat. No. 6,620,846, and U.S. patent application Ser. No. 09/919,877, filed Aug. 2, 2001, the entire disclosures of which are incorporated herein by reference.

The cyanoacrylates of this invention can be prepared according to several methods known in the art. U.S. Pat. Nos. 2,721,858, 3,254,111, 3,995,641, and 4,364,876, each of which is hereby incorporated in its entirety by reference herein, disclose methods for preparing cyanoacrylates.

As desired, the application according to this invention can include any of a wide variety of additional materials, either mixed into the polymerizable composition, or in a separate compartment from the polymerizable composition. Examples of suitable additional materials include, but are not limited to, plasticizing agents, thixotropic agents, thickeners, natural or synthetic rubbers, stabilizers, pH modifiers, bioactive agents, cross-linking agents, chain transfer agents, fibrous reinforcements, colorants, preservatives, formaldehyde reducing or scavenging agents, perfumes, mixtures thereof, and the like.

The adhesive material may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), polymethylmethacrylate, polydimethylsiloxane, hexadimethylsilazane, isopropyl myristate, isopropyl palmitate, and others as listed in U.S. Pat. No. 6,183,593, the disclosure of which is incorporated in its entirety by reference herein.

Suitable viscosities for the pre-polymer adhesive of the present invention is from 2 to 500 centipoise, the value depending on the use of the adhesive alone, in which case, a preferred range is 50-200 centipoise, or in the event that a mesh substrate is used with the adhesive, a suitable value is 100 centipoise+/−70 centipoise. The adhesive material may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. Nos. 4,720,513 and 6,310,166, the disclosures of which are hereby incorporated in their entireties by reference herein.

The adhesive material may optionally also include thickeners. Suitable thickeners may include poly (2-ethylhexyl methacrylate), poly (2-ethylhexyl acrylate) and others as listed in U.S. Pat. Nos. 6,183,593, and 6,310,166, the disclosures of which are incorporated by reference herein in their entirety.

The adhesive material may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The adhesive material may optionally also include one or more stabilizers, preferably both at least one anionic vapor phase stabilizer and at least one anionic liquid phase stabilizer. The composition may optionally also include, in addition to or in place of the anionic stabilizers, at least one free radical stabilizer. These stabilizing agents may inhibit premature polymerization. Suitable anionic and free radical stabilizers may include those listed in U.S. Pat. Nos. 6,183,593 and 6,512,023, the disclosures of which are incorporated by reference herein in their entirety.

However, as described above, a particular advantage of this invention, such as in embodiments where stabilizing materials are used, is that separate stabilizers can be omitted from the composition. Thus, in embodiments, the polymerizable composition preferably does not include any, or at least substantially none, additional stabilizer.

The adhesive material may also include pH modifiers to control the rate of degradation of the resulting polymer, as disclosed in U.S. Pat. No. 6,143,352, the entire disclosure of which is hereby incorporated by reference herein in its entirety.

Adhesive materials of this invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, all to Leung et al, which are hereby incorporated herein by reference in their entireties.

To improve the cohesive strength of adhesives formed from the adhesive materials of this invention, difunctional monomeric cross-linking agents may be added to the monomer compositions of this invention. Such cross-linking agents are known. U.S. Pat. No. 3,940,362 to Overhults, which is hereby incorporated herein in its entirety by reference, discloses exemplary cross-linking agents.

The adhesive materials of this invention may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, the disclosure of which is incorporated by reference herein in its entirety.

The polymerizable adhesive materials useful in this invention may also further contain one or more preservatives, for prolonging the storage life of the composition. Suitable preservatives, and methods for selecting them and incorporating them into adhesive compositions, are disclosed in U.S. Pat. No. 6,579,469, the entire disclosure of which is incorporated herein by reference.

In embodiments of this invention, the adhesive material and/or parts of the applicator/dispenser may contain additional materials such as a polymerization initiator, accelerator, rate-modifier, and/or cross-linking agent for initiating polymerization and/or cross-linking of the polymerizable monomer material. Such initiators, accelerators, rate-modifiers, and/or cross-linking agents can be included in the applicator tip, in a filter or plug within the applicator outlet or on any surface inside of the applicator where the liquid adhesive comes into contact, on the biologic or an organic mesh substrate or in the adhesive material, and/or elsewhere, as appropriate. Often mesh substrates may include a layer of adhesive to allow the mesh to first be held in place prior to the application of the adhesive of the present invention.

In embodiments of this invention, particularly where the adhesive material is not in contact with the applicator tip prior to use, it is possible to incorporate into the applicator tip additional components, such as polymerization initiators and/or accelerators, anesthetic, medicament, or the like, or even any of the various additives described above with respect to the polymerizable adhesive. This is advantageous, for example, where additional initiator or accelerator may be necessary to provide the desired cure rate of the adhesive once it is applied or where additional treatment is desired. Furthermore, this is advantageous in embodiments where additional stabilizers or polymerization inhibitors must be added to the adhesive composition in the assembly, so as to overcome the "cure speed loss" that often occurs when such stabilizing agents are added.

In embodiments, the initiator or accelerator material is an initiator and/or a rate modifier for polymerization and/or cross-linking of a polymerizable monomer. As used herein, a polymerization initiator is any material that causes a monomer composition applied to a substantially dry tissue (i.e., substantially in the absence of plasma or like tissue fluids) to polymerize in less than 300 seconds at ambient temperature, for example, at approximately 21-25° C. Preferably, the initiator causes the monomer composition to polymerize in less than 150 seconds at ambient temperature, more preferably within 60, 90 or 130 seconds. As used herein, a polymerization rate modifier is any material that changes the rate at which a polymerizable monomer would polymerize in the absence of that material. Preferably, the rate modifier accelerates the rate of the polymerization reaction, although for particularly fast-acting monomers it may decelerate that rate.

The material may be applied to the applicator tip, for example, by spraying, dipping, injecting, or brushing the applicator tip with a liquid medium containing the polymerization initiator or accelerator. It is preferably applied to the tip by dipping or injecting. For example, it may be applied to the tip by pumping of the liquid medium, for example, through a syringe, onto the tip. Methods of applying the polymerization initiator or accelerator to an applicator tip are described in more detail in U.S. Pat. No. 5,928,611 to Leung and U.S. patent application Ser. No. 09/069,979, filed Apr. 30, 1998, and Ser. No. 09/430,177, filed Oct. 29, 1999, and U.S. Pat. No. 6,217,603, the entire disclosures of which is incorporated herein by reference.

Particular initiators and accelerators for particular monomers may be readily selected by one of skill in the art without undue experimentation. Control of the molecular weight distribution of the applied adhesive can be enhanced by selection of the concentration and functionality of the initiator or accelerator vis-a-vis the selected monomer. Suitable polymerization initiators and accelerators for cyanoacrylate compositions include, but are not limited to, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide: anionic surfactants, including quaternary ammonium halides such as benzalkonium chloride or its pure components, and tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine, iodide and iodine and povidine; phosphines, phosphites and phosphonium salts, such as triphenylphosphine and triethyl phosphite; alcohols such as ethylene glycol; polyols including cellulosics; polyamines such as polyethyleneimine; methyl gallate; inorganic bases and salts, such as sodium bisulfite, magnesium hydroxide, calcium sulfate and sodium silicate; sulfur compounds such as thiourea and polysulfides: polymeric cyclic ethers such as monensin, nonactin, crown ethers (such as taught in U.S. Pat. Nos. 5,928,611 and 8,980,947), calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; water, aqueous solutions, aqueous dispersions, and any hydrated surface or surface functionalized surface, photoinitiators; and light or applied wave frequency energy and bioactive compounds or agents.

In preferred embodiments, the initiator may be a bioactive material, including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt naphthenate can be used as an accelerator for peroxide. Other suitable bioactive materials are disclosed in U.S. Pat. No. 5,928,611 to Leung and U.S. patent application Ser. No. 09/430,177, filed Oct. 29, 1999, and U.S. Pat. Nos. 6,217, 603 and 6,455,064, the entire disclosures of which is incorporated herein by reference.

The adhesive materials in this invention can also comprise a medicament. Inclusion of a medicament is often desirable in compositions intended for medical applications. The medicament can either be added to the monomer-containing adhesive composition prior to packaging, or, alternatively, to the applicator tip or other part. Thus, the medicament may be applied to a tissue prior to or simultaneously with application of the monomer-containing adhesive composition. In addition to serving its medicinal function, the medicament may be selected so that it functions in conjunction with the co-packaged polymerizable monomer composition to initiate polymerization of the monomer or modify (e.g., accelerate) the rate of polymerization for the monomer to form a polymeric adhesive. The proper combination of medicament and polymerizable monomer can be determined easily by one of skill in the art. The medicament is supplied in an amount that will be pharmaceutically effective when applied topically (i.e., directly to tissue).

Examples of such medicaments include, but are not limited to antibiotics, antimicrobials, antiseptics, bacteriocins, bacteriostats, disinfectants, steroids, anesthetics, fungicides, anti-inflammatory agents, antibacterial agents, antiviral agents, antitumor agents, growth promoters, and mixtures thereof.

The medicament can have a pharmaceutical effect only at the site of application (i.e., limited to the tissue on/in which it is applied), or it can have a systemic effect (by systemic, it is not only meant that the medicament has an effect throughout the patient's body, but also at a specific site other than the site of application). In embodiments where the medicament is applied in an amount sufficient to show a systemic pharmaceutical activity, it can be absorbed, transported, or otherwise distributed to the site or sites within the patient where the pharmaceutical activity is desired, e.g., through the cardiovascular or lymph systems. The medicament may be in the tip or on the outside of the ampoule in form of a solid, such as a powder or a solid film, or in the form of a liquid, such as a watery, viscous, or paste-like material. The medicament may also be compounded with a variety of additives, such as surfactants or emulsifiers, and vehicles.

The polymerizable and/or cross-linkable material may be neat (no additional compounds added) or in a solvent, emulsion or suspension. Suitable solvents according to this invention include alcohol, ether alcohol, hydrocarbons, halogenated hydrocarbons, ethers, acetals, ketones, esters, acids, sulfur- or nitrogen-containing organic compounds, mixtures thereof and the like. Other suitable solvents are disclosed in U.S. Pat. No. 5,130,369 to Hughes et al. and U.S. Pat. No. 5,216,096 to Hattori et al., the entire disclosures of which are incorporated herein by reference. These solvents may be used either independently or in combination of two or more. They may also be used in conjunction with water to the extent that the polymerizable and/or cross-linkable material is dissolved or suspended in such a mixture. The total amount of solvent that may be incorporated into the polymerizable and/or cross-linkable material may be 0 to 99, preferably 1 to 50, and more preferably 3 to 25 percent by weight. Selection of the amount will, of course, depend on the desired monomer and process conditions, and amounts outside these ranges may be acceptable.

In embodiments, the monomer composition and/or its packaging are preferably sterilized and can be provided in a sterilized condition in the ampoule of the system of the invention or can be sterilized after assembly. Sterilization of the monomer composition and/or its packaging can be accomplished by techniques known to one of ordinary skill in the art, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of dry sterilization achieves sterility of $10^{-6}$ over the range of conditions proposed for routine processing as disclosed and incorporated U.S. Pat. No. 8,808,620. Examples of irradiation methods include, but are not limited to, gamma irradiation, electron beam irradiation, UV, IR and microwave irradiation. A method of electron beam irradiation, as described in U.S. Pat. No. 6,143,805, the entire disclosure of which is incorporated herein by reference. The composition must show low levels of toxicity to living tissue during its useful life. In preferred embodiments of this invention, the composition is sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$. Further details of sterilization are disclosed in incorporated U.S. Pat. No. 6,779,657.

It should be understood that the individual features of the various exemplary embodiments may be included or excluded as desired for a given application. As such, all possible combinations of the described features are considered to be encompassed by this invention.

Thus, while this invention has been described in terms of exemplary embodiments, it is to be understood that this invention is not to be limited to the particular configuration of these embodiments. One skilled in the art will recognize that various modifications and/or alterations of these embodiments maybe made while remaining within the scope of this invention.

What is claimed is:

1. An applicator for a material in a breakable ampoule, comprising:

a body portion having a long axis and which defines a cavity to contain the breakable ampoule, wherein the cavity includes a breaking member and a ramp feature which opposes the breaking member along the long axis, a material dispensing opening in communication with the cavity, wherein the material dispensing opening is configured to dispense the material from the applicator to a site of application on a body; and an actuator member configured to act on the breakable ampoule to move the breakable ampoule in the direction of the long axis which causes the breakable ampoule to engage the breaking member to allow the material to access the material dispensing opening, wherein the actuator member is configured to control the flow of the material out of the applicator through the material dispensing opening, and wherein when pressure is applied to the actuator member the material flows out of the material dispensing opening and when the pressure applied to the actuator member is released the material stops flowing out of the material dispensing opening via a spring force generated by the actuator member that acts in contravention to the pressure applied by a user;

wherein an upper end of the breakable ampoule is contained in a cap member coupled to the actuator member through a linkage which extends directly from the actuator member to the cap member, and wherein the cap member is located entirely within the cavity of the body portion.

2. The applicator as set forth in claim 1, wherein the body portion has a distal end and a proximal end along the long axis, wherein the material dispensing opening is in the distal end of the body portion, wherein the breakable ampoule is received in the cavity, wherein the breaking member is in a portion of the cavity in the distal end of the body portion, and wherein the breakable ampoule is present between the breaking member and the cap member.

3. The applicator as set forth in claim 2, wherein the ramp feature is across the long axis from the breaking member so that the breakable ampoule is configured to be loaded along the long axis into the breaking member by the ramp feature.

4. The applicator as set forth in claim 1, wherein the actuator member further includes an integral spring member that is configured to apply the spring force in opposition to the pressure on the actuator member.

5. The applicator as set forth in claim 4, wherein the spring member is a spring arm and is integral with the linkage of the actuator member.

6. The applicator as set forth in claim 1, wherein the actuator member further includes a handle member operatively connected to the linkage, wherein the linkage is operatively connected to the cap member in which the upper end of the breakable ampoule is present, and wherein when the handle member is depressed, the breakable ampoule moves in the direction of the long axis towards the material dispensing opening.

7. The applicator as set forth in claim 6, wherein the actuator member further includes a spring member integrally connected to the handle member, wherein the spring member opposes pivoting pressure of the handle member toward the body portion and is configured such that when the user releases the handle member, the handle member in turn stops pressure on the cap member and stops the flow of the material out of the material dispensing opening.

8. The applicator as set forth in claim 7, wherein the actuator member is pivotally connected to the body portion at a proximal end of the body portion.

9. The applicator as set forth in claim 8, wherein the pivotal connection is provided by a boss of the actuator member and a recess of the body portion.

10. The applicator as set forth in claim 9, wherein the applicator further includes a filter member situated between the breakable ampoule and the material dispensing opening within the body portion.

11. The applicator as set forth in claim 10, wherein the material is an adhesive.

12. An applicator for a material in a breakable ampoule, comprising:

a body portion having a long axis and which defines a cavity to contain the breakable ampoule, wherein the cavity includes a breaking member and a ramp feature, a material dispensing opening located at a distal end of the body portion and being in communication with the cavity, wherein the material dispensing opening is configured to dispense the material from the applicator to a site of application on a body; and an actuator member configured to act on the breakable ampoule to move the breakable ampoule in the direction of the long axis which causes the breakable ampoule to engage the breaking member to allow the material to access the material dispensing opening, wherein the actuator member includes a) a cap member located in the cavity that holds the breakable ampoule and forms a seal with the body portion, b) a handle member which pivots about a hinge axis and acts on a lever linkage coupled to the cap member, and c) a counter spring member which acts to bias the handle member against pressure applied to the handle member, wherein when the pressure is applied to the handle member the material flows out of the material dispensing opening and when the pressure applied to the actuator member is released the material stops flowing out of the material dispensing opening via a spring force generated by the counter spring member that acts in contravention to the pressure applied by a user;

wherein an upper end of the breakable ampoule is contained in a cap member coupled to the actuator member through a linkage which extends directly from the actuator member to the cap member, and wherein the cap member is located entirely within the cavity of the body portion.

13. The applicator as set forth in claim 12, wherein the actuator member is configured to cause the material to be drawn back into the applicator at the material dispensing opening via the spring force generated by the counter spring member.

14. The applicator as set forth in claim 12, wherein the ramp feature is across the long axis from the breaking member so that the breakable ampoule is configured to be loaded along the long axis into the breaking member by the ramp feature.

15. The applicator as set forth in claim 14, wherein the actuator member is pivotally connected to the body portion at a proximal end of the body portion.

16. The applicator as set forth in claim 15, wherein the pivotal connection is provided by a boss of the actuator member and a recess of the body portion.

17. The applicator as set forth in claim 16, wherein the applicator further includes a filter member situated between the breakable ampoule and the material dispensing opening within the body portion.

18. The applicator as set forth in claim 17, wherein the material is an adhesive.

\* \* \* \* \*